United States Patent [19]
Herstein

[11] Patent Number: 5,902,591
[45] Date of Patent: May 11, 1999

[54] STABLE TOPICAL COSMETIC/ PHARMACEUTICAL EMULSION COMPOSITIONS CONTAINING ASCORBIC ACID

[75] Inventor: Morris Herstein, Scarsdale, N.Y.

[73] Assignee: La Prairie SA, Volketswil, Switzerland

[21] Appl. No.: 08/832,938

[22] Filed: Apr. 3, 1997

[51] Int. Cl.⁶ ..................................................... A61K 7/00
[52] U.S. Cl. ........................... 424/401; 424/59; 514/770; 514/873; 514/887; 514/937; 514/970; 514/939
[58] Field of Search ..................... 424/401, 59; 514/770, 514/873, 887, 937, 970, 939

[56] References Cited

U.S. PATENT DOCUMENTS

| | | | |
|---|---|---|---|
| 2,400,171 | 5/1946 | Ruskin | 167/81 |
| 2,442,461 | 6/1948 | Karrer et al. | 167/81 |
| 2,531,427 | 11/1950 | Hauser | 260/448 |
| 2,585,580 | 2/1952 | Opplt | 260/344.5 |
| 2,966,506 | 12/1960 | Jordan | 260/448 |
| 3,755,560 | 8/1973 | Dickert et al. | 424/78 |
| 3,945,939 | 3/1976 | Barron | 252/182 |
| 4,130,607 | 12/1978 | Arold | 260/973 |
| 4,254,105 | 3/1981 | Fukuda | 424/170 |
| 4,367,157 | 1/1983 | Sherman | 252/106 |
| 4,372,874 | 2/1983 | Modrovich | 436/176 |
| 4,421,769 | 12/1983 | Dixon et al. | 424/358 |
| 4,557,934 | 12/1985 | Cooper | 424/128 |
| 5,487,884 | 1/1996 | Bissett et al. | 424/59 |
| 5,618,522 | 4/1997 | Kaleta et al. | 424/60 |

FOREIGN PATENT DOCUMENTS

| | | |
|---|---|---|
| 2035086 | 7/1991 | Canada . |
| 2101101 | 2/1994 | Canada . |
| 0 303 461 A1 | 2/1989 | European Pat. Off. . |
| 0 679 387 A1 | 11/1995 | European Pat. Off. . |
| WO 96/07396A2 | 3/1996 | WIPO . |

OTHER PUBLICATIONS

International Cosmetic Ingredient Dictionary, p. 867, Jan. 1998.

The Colloid Chemistry of Silica and Silicates, Ralph K. Iller, Cornell University Press, 1955, pp. 223–228.

*Primary Examiner*—Thurman K. Page
*Assistant Examiner*—James M. Spear
*Attorney, Agent, or Firm*—Sprung Kramer Schaefer & Briscoe

[57] ABSTRACT

Stable topical emulsions for cosmetic/pharmaceutical purposes can be made from a two component system of a powdered ascorbic acid phase and a liquid phase, the liquid phase containing an emulsion stabilizingly effective amount of an organoclay material.

24 Claims, No Drawings

STABLE TOPICAL COSMETIC/PHARMACEUTICAL EMULSION COMPOSITIONS CONTAINING ASCORBIC ACID

BACKGROUND OF THE INVENTION

The present invention relates to stable topical cosmetic/pharmaceutical emulsion compositions containing ascorbic acid. More particularly, the invention relates to topical emulsion compositions containing ascorbic acid (vitamin C) which are stabilized by means of certain clay/cationic surfactant combinations.

Considerable effort has been expended to find ways to prevent adverse changes in the skin brought about by environmental conditions such as ultraviolet (UV) exposure. Ascorbic acid has many known biological functions from enzymatic co-factor to "sparing" agent against vitamin E depletion. The latter function may partly account for its "anti-oxidant" status. Additionally, at higher concentrations, ascorbic acid is known to react with both superoxide and hydroxyl radicals. Superoxide and the subsequently generated hydrogen peroxide and hydroxyl radical are oxygen-containing free radicals now known to be generated in vivo under a variety of normal and pathological conditions. Quite simply, these radicals have been implicated as causative agents for everything from sunburn to aging. These radicals destroy lipid membranes, break down DNA, inactivate enzymes and so forth. An immense amount of work has been done in the last two decades documenting the deleterious behavior of oxygen radicals.

L-Ascorbic acid (or vitamin C) is chemically defined as an α-keto-lactone with the following structure:

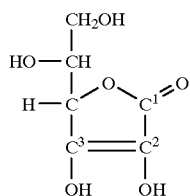

The number 2 and 3 carbons are double-bonded and contain an acid-ionizable hydrogen in water (pK=4.2). Ascorbic acid is also a moderately strong reductant. These properties, which lead to instability in the ascorbic acid structure, are well known and have been burdensome to pharmacologists when attempting to formulate active ascorbic acid solutions. Thus, at higher pH's, the ascorbic acid increasingly becomes the notoriously unstable ascorbate anion. This instability may be due to several causes not restricted to:

a) Stereochemical strain due to polar repulsive forces. Thus, when the 2-hydroxy group ionizes, it places two negative charges (the other being on the carboxyl oxygen) in close proximity which favors ring disruption.

b) Oxidative degradation due to the ascorbate anion's propensity to act as a reductant. The one-electron oxidation product (dehydroascorbate free radical) tends to disproportionate, forming another ascorbate molecule and the two-electron oxidation product, dehydroascorbate, which is extremely unstable in aqueous solution and breaks down to ultimately form species such as L-threonic acid and oxalic acid. Transition metal ions can catalyze these reactions.

c) Degradation due to water attack. At lower ascorbic concentrations or ionic strength, water itself can react with and degrade the ascorbate molecule.

For these reasons, among others, scientists working in the field have had difficulty in formulating stable solutions of ascorbic acid which would be useful for cosmetic or dermatological needs. Nevertheless, because of the many beneficial pharmaceutical effects attributed to ascorbic acid, numerous attempts have been made to overcome these difficulties.

Thus, the literature describes ascorbic acid compositions formed by using a very low weight percent ascorbic acid, or a nonaqueous solvent, or by using derivatives of ascorbic acid, usually in a solution buffered to a pH above 4.0. Also, see, for example, Takashima et al, "Ascorbic Acid Esters and Skin Pigmentation," Am. Perfumer & Cosmetics 86: 29 (July 1971) (esterifying the hydroxyl group to form ascorbic acid-3-phosphate and maintaining an alkaline pH); Ciminera and Wilcox, "Stable Ascorbic Acid Solution for Parenteral Use", J. Am. Pharm. Assoc. Sci. Ed. 35: 363 (1946) (buffering an aqueous solution with an alkaline sodium salt). See also U.S. Pat. No. 4,367,157 which discloses stabilizing an aqueous ascorbic acid solution by adding monothioglycerol and maintaining the pH between 4 and 7; U.S. Pat. No. 2,400,171 which discloses stabilizing ascorbic acid by converting it to its calcium or zinc salt and preferably maintaining the pH at 7 to 7.3; U.S. Pat. No. 2,442,461 which discloses stabilizing calcium ascorbate by adding an aliphatic thiocarboxylic acid and maintaining the pH between 5.2 and 5.6; U.S. Pat. No. 2,585,580 which discloses stabilizing ascorbic acid with thio-sugars and maintaining the pH between 4.0 and 6.5; and U.S. Pat. No. 4,372,874 which discloses actually removing the water to below 0.5 wt. % by using a desiccant. In many cases, these techniques have been successful in obtaining stable solutions but have been reasonably expensive and have yielded a product with less desirable properties than ascorbic acid in its unmodified form.

In addition, many of the cosmetic and dermatological topical formulations are in the form of emulsions. In addition to the known instability of ascorbic acid in water, the acidity introduced by the ascorbic acid has the effect of breaking down emulsions almost immediately at elevated temperature and over a few days at room temperature.

One method of overcoming the tendency of the ascorbic acid to break emulsion is by the use of a carrier containing a hydrophilic gelling agent in the water phase of the emulsion. The product is designed so that upon use, the ascorbic acid powder is added to an aqueous carrier containing the hydrophilic gelling agent and the product is shaken to mix the two. The hydrophilic gelling agents used generically include polysaccharides, synthetic polymers, and celluloses, e.g., carrageenan, guar, xanthan, celluloses such as hydroxyalkylcellulose and sodium carboxycellulose, gelatin, agar—agar, and amidon. This is disclosed in EP 0 679 387.

SUMMARY OF THE INVENTION

It has now been discovered that a new, stable topical emulsion composition containing ascorbic acid, preferably from about 0.1 to 20 wt. %, more preferably about 2 to 10 wt. % and more particularly form about 4% to about 8% ascorbic acid based on the weight of the final composition can be obtained by using the ascorbic acid in combination with an emulsion composition containing a stabilizing effective amount of an organoclay composition. Topical emulsions can be prepared whereby the emulsion are stable for up to 15 days.

DETAILED DESCRIPTION OF THE INVENTION

The present invention provides topical cosmetic/pharmaceutical emulsion compositions that are provided in two phases, i.e., a powder phase containing ascorbic acid and a liquid emulsion phase containing a stabilizingly effective amount of an organoclay composition. Upon mixing at the point of use, the emulsion remains stable and doesn't break and the ascorbic acid remains stable for about two weeks (stability being equated with less than 10% loss).

Ascorbic Acid

The ascorbic acid is generally used in pure powder form though carriers, dyes, pigments, fillers, flow control agents, desiccants and other cosmetic adjuvants can be used if desired. A solution such as in a cosmetically or pharmaceutically acceptable solvent that does not degrade the ascorbic acid could also be used.

As one skilled in the art would recognize, the ascorbic acid may be provided by the addition of any cosmetically/pharmaceutically acceptable salt or ester. Also, any reducing analog of ascorbic acid, such as D-isoascorbic acid or perhaps by the addition of other small reducing compounds such as, but not limited to, glutathione, L-cysteamine, etc. could be used. Such forms would be expected to provide an equivalent composition to that claimed and are within the scope of the invention.

The organoclay material used in the invention which can also be defined as an anion cation modified clays can be defined by the formula:

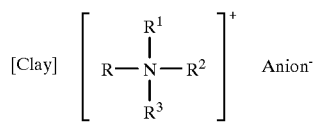

wherein clay represents an aluminium silicate, more properly a hydrated aluminium silicate alone or in admixture with other clays. The prefered anion is the chloride.

Preferably, the clay is bentonite. A major component of bentonite is montmorillonite. Montmorillonite is a major component of fuller's earth. Attapulgite, an aluminium magnesium silicate is also a component of fuller's earth. Hectorite, a sodium magnesium lithium silicate is also a component of montmorillonite. Other aluminium silicates include halloysite and koalinite, a major component of kaolin. These clays, alone or in combination, can be used in the present invention to the extent they form complexes with onium compounds, particularly quaternary cationic surfactants.

In the formula, R represents a fatty radical of $C_{10}$ to $C_{20}$. $R^1$, $R^2$ and $R^3$ represent independently R or a lower alkyl or hydroxyalkyl radical ($C_1$–$C_4$). Preferably, R and $R^1$ represent hydrogenated tallow fatty radicals. Other representative fatty radicals include coconut. The carbon chain length is intended to include compounds with mixed carbon chains. Preferably, $R^2$ and $R^3$ are independently methyl or hydroxyethyl.

The preferred clays for use in this invention are such naturally occurring minerals as bentonites and montmorilonites containing inorganic cations which are rather easily replaced by substituted ammonium ions. The modified clays are prepared by reacting a sodium, potassium, magnesium or similar type of bentonite-like clay with a substituted ammonium base salt, such as dimethyl benzyl hydrogenated tallow ammonium chloride, whereby the dimethylbenzyl-hydrogenated tallow ammonium salt of the clay is formed. Alternatively, an acidic bentonite-like clay may be reacted with a substituted ammonium base such as decylamine to produce the organophilic ammonium cation-modified clay.

These modified clays have a property of swelling several times their original volume in the presence of relatively polar organic solvents and are capable of thickening these relatively polar solvents.

In addition to ammonium cation-modified clays, various onium cation modified clays suitable for use in the present invention are described in U.S. Pat. No. 2,531,427 which was issued Nov. 28, 1950, to Ernest A. Hauser and U.S. Pat. No. 2,966,506 issued Dec. 27, 1960 to J. W. Jordan, incorporated herein by reference. Examples of such materials are montmorillonites, bentonites, zeolites, attapulgites, etc. Originally these clays were in the form of acidic or inorganic salts but have been converted into onium salts by reaction with an onium compound in which the onium radical is selected from the class consisting of ammonium, phosphonium, oxonium, sulfonium, seleneonium, stannonium, arsonium, stibonium, telluronium, and iodonium and has at least one alkyl substituent of at least 10 carbon atoms. The other onium cationic modified clays may be utilized in this invention in place of the ammonium cationic modified clays, although the latter are preferred.

Modified clays can be illustrated by a hectorite clay modified with dimethyl dihydrogenated tallow ammonium chloride, a Wyoming Bentonite clay modified with dimethyl dihydrogenated tallow ammonium chloride, a hectorite clay modified with dimethyl benzyl hydrogenated tallow ammonium chloride, and a Wyoming Bentonite clay modified with dimethylbenzyl hydrogenated tallow ammonium chloride, mixtures thereof and the like. The organoclay is used in a ratio to the ascorbic acid of from 0:01 to 1:1 and preferably from 0.05 to 0.5:1.

The Liquid Phase

The water used in preparing the compositions of the invention is preferably distilled and/or deionized, but any water may be used which does not contain contaminants which would affect the stability of the ascorbic acid composition. The effects of water of varying purity on ascorbic acid stability is discussed in Meucci et al., "Ascorbic Acid Stability in Aqueous Solutions," Acta Vitaminol. Enzymol. 7(3-4): 147–54 (1985), incorporated herein by reference.

A metal chelator, illustrated by diethylene triaminepentaacetic acid (DTPA) or ethylenediamine-di(o-hydroxyphenylacetic acid) (EDDHA), or ethylenediamine tetraacetic acid (EDTA) can be added to the composition in minor amounts (0.001% to 0.1% (w/v) to provide additional stability to the ascorbic acid, particularly when used at the lower concentration.

The ascorbic acid is used in combination with both pharmaceutically-acceptable and cosmetically-acceptable safe ingredients sufficiently high in purity and sufficiently low in toxicity to render them suitable for application to the skin of animals and humans. In addition, non-irritating components are used which are suitable for delivering the ascorbic acid to the skin. The components must be capable of being commingled with the ascorbic acid and the other ingredients in such a manner that there is no adverse interaction which would substantially reduce the efficacy of the composition during use. Variation in the liquid phase ingredients will result in the production of a wide range of products falling within the groups of pharmaceutical/cosmetic, and cleaning compositions. These products may be in the form of a wide variety of product types such as liquid, lotions, creams, sprays, sticks, ointments, pastes, and cosmetics.

Emulsifiers

As the liquid phase is in the form of an emulsion, from about 1% to about 10%, preferably from 3% to about 8% of the liquid phase comprises an emulsifier. Emulsifiers can be nonionic, anionic or cationic. Suitable emulsifiers are disclosed in U.S. Pat. Nos. 3,755,560, 4,421,769, and McCutcheon's Detergents and Emulsifiers, North American Edition, pages 317–324 (1986), the disclosures of which are incorporated herein by reference. The preferred types of emulsifiers are nonionic and anionic.

Examples of useful nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid asters of ethylene glycol wherein the fatty acid moiety contains from 10 to 20 carbon atoms, fatty acid monoglycerides wherein the fatty acid moiety contains from 10 to 20 carbon atoms, diethylene glycol, polyethylene glycols of molecular weight 200 to 6000, propylene glycol of molecular weight 200 to 3000, sorbitol, sorbitan and polyoxyethylene sorbitol. Examples of such emulsifiers include polyoxyethylene (2 or 8 or 21) stearate, myristyl ethoxy (3) myristate, polyoxyethylene (100) monostearate, octyl and glyceryl stearate, lauric diethanolamide, stearic monoethanolamide, hydrogenated vegetable glycerides, and sodium stearoyl-2-lactylate.

Suitable anionic emulsifiers include the fatty acid soaps, e.g., sodium, potassium, and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units.

Cationic emulsifiers useful in the present invention include quaternary ammonium, morpholinium and pyridinium compounds. Examples of such emulsifiers include dialkyl ($C_{12}$–$C_{18}$) quaternary ammonium salts, cetyl trimethyl ammonium salts; alkyl dimethyl benzyl ammonium salts, and cetyl pyridinium salts.

Also usable in the invention are such natural emulsifiers as lecithin.

Single emulsion skin care preparations, such as lotions and creams, of the oil-in-water type and water-in-oil type are well known in the cosmetic art and are useful in the present invention. Multiphase emulsion compositions, such as the water-in-oil-in-water type, as disclosed in U.S. Pat. No. 4,254,105, Fakuda et al., issued Mar. 3, 1981, herein incorporated by reference, are also useful in the present invention.

Emulsion systems comprising water-in-silicone fluid emulsion compositions are also useful in the present invention. More particularly, such emulsion systems comprise (a) from about 15% to about 90% by weight (of the liquid phase) of a silicone fluid continuous phase consisting essentially of at least one liquid organopolysiloxane, (b) from about 30% to about 80% by weight (of the liquid phase) of an aqueous discontinuous phase comprising an oil-in-water emulsion of a cosmetically-acceptable oily liquid nonparticulate phase dispersed in an aqueous phase, and (c) from about 0.5% to about 5% by weight (of the vehicle) of an effective dispersing amount of dimethicone copolyol for dispersing (b) in (a).

Preferably said liquid organopolysiloxane consists of one or more volatile organopolysiloxanes selected from the group consisting of octamethylcyclotetrasiloxane, decamethylcyclopentasiloxane, dodecamethylcyclohexasiloxane, cyclomethicone, and hexamethyldisiloxane in a mixture with one or more nonvolatile organopolysiloxanes selected from the group consisting of: dimethicone copolyol, dimethylpolysiloxane, diethylpolysiloxane, mixed $C_1$–$C_3$ alkyl polysiloxane, phenyl dimethicone and a high molecular weight dimethicone having an average molecular weight of from about 200,000 to about 1,000,000, in a respective weight ratio of from about 5:1 to about 25:1, and said oily phase comprises heavy mineral oil, cholesterol and cetyl palmitate in a respective weight ratio of about 10:5:1.

Another emulsion system useful in the pharmaceutical/cosmetic compositions of the present invention is a microemulsion system. Such a system comprises from about 9% to about 15% squalane; from about 25% to about 40% silicone oil; from about 8% to about 20% of fatty alcohol; from about 15% to about 30% of polyoxyethylene sorbitan non-fatty acid (commercially available under the trade name Tweens) or other nonionics; and from about 7% to about 20% water. This system can be combined with from about 2% to about 10% ascorbic acid.

Lotions and creams can be formulated as emulsions. Typically such lotions comprise from about 1% to about 20%, preferably from about 2% to about 10% ascorbic acid; from about 1% to about 20%, preferably from about 5% to about 10%, of one or more emollients; from about 25% to about 75%, preferably from about 45% to about 95%, water; and from about 1% to about 10%, preferably from about 2% to about 5%, of emulsifier. Creams would typically comprise from about 1% to about 20%, preferably from about 2% to about 10%, ascorbic acid; from about 1% to about 20%, preferably from about 5% to about 10%, of one or more emollients; from about 20% to about 80%, preferably from about 30% to about 70%, water; and from about 1% to about 10%, preferably from about 2% to about 5%, of one or more emulsifiers.

If the pharmaceutical/cosmetic emulsion compositions of the invention are formulated as a gel or a cosmetic stick, a suitable amount of a cosmetic thickening agent such as hydrocolloids, cellulose derivatives and high molecular weight synthetic polymer, is added to a cream or lotion formulation.

The pharmaceutical/cosmetic compositions of the invention may contain, in addition to the aforementioned components, a wide variety of additional oil-soluble materials and/or water-soluble materials conventionally used in topical compositions, at their art-established levels.

Among the optional oil-soluble materials are nonvolatile silicone fluids, such as polydimethyl siloxanes with viscosities ranging from about 10 to about 100,000 centistokes are 25° C. These siloxanes are useful to enhance skin feel and are available from Dow Corning Corporation as the Dow Corning 200 series. These optional oil-soluble materials may comprise up to about 20% of the total composition, preferably up to about 10%.

Various water-soluble materials may also be present in the compositions of this invention. These include humectants, such as glycerol, sorbitol, propylene glycol, alkoxylated glucose and hexanetriol, polyvinyl alcohol, and clays such as Veegum, ® (magnesium aluminum silicate, R. T. Vanderbilt, Inc.); proteins and polypeptides; preservatives such as the methyl, ethyl, propyl and butyl esters of hydroxybenzoic acid (Parabens-Mallinckrodt Chemical Corporation), EDTA, methylisothiazolinone and imidazolidinyl ureas (Germall 115—Sutton Laboratories) phenoxyethanol, chlorphenesin; and an alkaline agent such as sodium hydroxide or potassium hydroxide to neutralize, if desired, part of the fatty acids or thickener which may be present.

The topical composition herein can also contain conventional cosmetic adjuvants, such as dyes, opacifiers (e.g., titanium dioxide), pigments and perfumes.

The pharmaceutical/cosmetic compositions of the present invention may also include a safe an effective amount of a penetration enhancing agent. By "safe and effective amount" is meant an amount sufficient to enhance penetration of the ascorbic acid into the skin but not so much as to cause any side effects or skin reactions, generally from about 1% to about 5% of the composition. Examples of useful penetration enhancers, include a penetration-enhancing vehicle consisting essentially of (a) N-(2-hydroxyethyl)-pyrrolidone and (b) a cell envelope disordering compound selected from methyl laurate, oleic acid, oleyl alcohol, monoolein, myristyl alcohol, and mixtures thereof, wherein component (a) and (b) are present in a ratio of (a):(b) of about 1:5 to about 500:1 by weight. U.S. Pat. No. 4,557,934 teaches a pharmaceutical composition comprising the penetration enhancing agent 1-dodecylazacycloheptan-2-one, and a penetration enhancing diol or cycloketo compound selected from the group consisting of: 1,2-propanediol, 1,3-propanediol, 1,2-butanediol, pyrrolidone; 1-(2-hydroxyethyl)azacyclopentan-2-one, and mixtures thereof. U.S. Pat. No. 4,130,667 describes a penetration enhancer comprising:

(a) at least about 0.1% by weight of a sugar ester selected from sucrose monooctanoate, sucrose monodecanoate, sucrose monolaurate, sucrose monomyristate, sucrose monopalmitate, sucrose monostearate, sucrose monooleate, and sucrose dioleate; and (b) at least about 0.1% by weight of a phosphine oxide compound selected from octyl or monyl or decyl or undecyl or dodecyl-dimethyl phosphine oxide, and the 2-hydroxydecyl derivative thereof.

Other conventional skin care product additives may also be included in the compositions of the present invention. For example, collagen, hyaluronic acid and its salts, elastin, hydrolysates, primrose oil, jojoba oil, epidermal growth factor, soybean saponins, mucopolysaccharides, and mixtures thereof may be used.

Various vitamins may also be included in the compositions of the present invention. For example, Vitamin A and derivatives thereof, Vitamin $B_2$, biotin, pantothenic acid, Vitamin D, Vitamin E and mixtures thereof may be used.

The compositions of the present invention can also contain from about 2% to about 50% of at least one pharmaceutically/cosmetically acceptable emollient. Various types of emollients are known, depending on whether the emollient is in the aqueous or the oil phase of the emulsions.

As used herein, "emoilients" refer to materials used for the prevention or relief of dryness, as well as for the protection of the skin. A wide variety of suitable emollients are known and may be used herein. Sagarin, *Cosmetics, Science and Technology*, 2nd Edition, Vol. 1, pp., 32–43 (1972), incorporated herein by reference contains numerous examples of suitable materials. Examples of classes of useful emollients include the following:

1. Hydrocarbon oils and waxes. Examples include mineral oil, petrolatum, microcystalline wax, polyethylene, and perhydrosqualene. Also included in this group is wax esters such as beeswax, spermaceti, myristyl myristate, stearyl, stearate and the derivatives thereof such as ethoxylated sorbitol beeswax ether-esters. Further included are vegetable waxes including carnauba and candelilla waxes.
2. Silicone oils, such as dimethyl polysiloxanes, methylphenyl polysiloxanes, water-soluble and alcohol-soluble silicone glycol copolymers including dimethicone and trimethicone.
3. Triglyceride esters, for example vegetable and animal fats and oils including oils of castor, safflower, cottonseed, corn, cod liver, palm, sesame, and soybean.
4. Acetoglyceride esters, such as acetylated monoglycerides.
5. Ethoxyiated glycerides, such as ethoxylated glyceryl monostrearate.
6. $C_1$–$C_{20}$-alkyl esters of fatty acids having 10 to 20 carbon atoms such as laurates, palmitates, oleates, stearates, adipates, sebacates, and lauryl lactates.
7. Alkenyl esters of fatty acids having 10 to 20 carbon atoms. Examples include oleyl myristate, oleyl stearate, and oleyl oleate.
8. Fatty acids having 10 to 20 carbon atoms. Suitable examples include pelargonic, lauric, myristic, paimitic, stearic, isostearic, hydroxystearic, oleic, linoleic, ricinoleic, arachidic, behenic, and eruric acids.
9. Fatty alcohols having 10 to 20 carbon atoms. Lauryl, myristyl, cetyl, hexadecyl, stearyl, isostearyl, hydroxystearyl, oleyl, ricinoleyl, behenyl, and erucyl alcohols, as well as 2-octyl dodecanol, are examples of satisfactory fatty alcohols.
10. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups.
11. Ether-esters such as fatty acid esters of ethoxylated fatty alcohols.
12. Lanolin and Sterol and derivative thereof. Lanolin, lanolin oil, lanolin wax, lanolin alcohols, lanolin fatty acids, hydrogenated of lanolin, and ethoxylated, propoxyated and acetylated derivatives thereof, and liquid and semisolid lanolin absorption bases are illustrative of emollients derived from lanolin. Also included in this group are sterols. Cholesterol and cholesterol fatty acid esters are examples thereof.
13. Polyhydric alcohols and polyether derivatives exemplified by propylene glycol, dipropylene glycol, polypropylene glycols 2000 and 4000, polyoxyethylene polyoxypropylene glycols, glycerol, sorbitol, ethoxylated sorbitol, polyethylene glycols 200–6000, poly(ethylene oxide) homopolymers (100,000–5,000,000), polyalkylene glycols and derivatives, 1,3-butylene glycol, 1,2,6-hexanetriol, ethohexadiol USP (2-ethyl-1,3-hexanediol), $C_{15}$–$C_{18}$ vicinal glycol, and polyoxypropylene derivatives of trimethylolpropane and the fatty esters ($C_{10}$–$C_{20}$) thereof.
14. Phospholipids, such as lecithin and derivatives.
15. Amides such as fatty acid amides, ethoxylated fatty acid amides, solid fatty acid alkanolamides.

Particularly useful emollients which provide skin conditioning are glycerol, hexanetriol, butanetriol, lactic acid and its salts, urea, pyrrolidone carboxylic acid and its salts, amino acids, guanidine, diglycerol and triglycerol. Preferred skin conditioning agents are the propoxylated glycerol derivatives disclosed in U.S. patent application Ser. No. 023,059, Orr et al., filed Mar. 6, 1987 U.S. Pat. No. 4,976, 953. These agents preferably have a formula selected from:

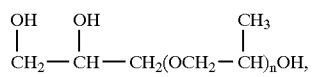

-continued

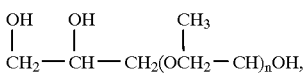

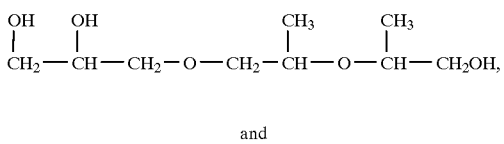

and

OH  OH           CH₃              CH₃
|   |            |                |
CH₂—CH—CH₂—O—CH—CH₂—O—CH₂—CH—OH, wherein n=1 or 2, and mixtures thereof.

Sunscreens

A wide variety of conventional sunscreening agents are suitable for use in the present invention. Segarin, et al., at Chapter VIII, Pages 189 et seq., of *Cosmetics Science and Technology*, disclose numerous suitable agents, the disclosure of which is incorporated herein by reference. Specific suitable sunscreening agents include, for example:

p-aminobenzoic acid, its salts and derivatives, anthranilates, salicylates, cinnamic acid derivatives, dihydroxycinnamic acid derivatives, trihydroxycinnamic acid derivatives, hydrocarbons, dibenzalacetone and benzalacetophenone, naphthosulfonates, dihydroxynaphthoic acid and its salts, o- and p-hydroxybiphenyldisulfonates, coumarin derivatives, diazoles quinine salts, quinoline derivatives, hydroxy or methoxy substituted benzophenones, uric and vilouric acids, tannic acid and its derivatives, hydroquinone, benzophenones, and the like.

The pharmaceutical/cosmetic emulsion compositions of the present invention typically include a pharmaceutically- or cosmetically-acceptable organic solvent. The terms "pharmaceutically-acceptable organic solvent" and "cosmetically-acceptable organic solvent" refer to an organic solvent which, in addition to being capable of having dispersed or dissolved therein the oil soluble ingredients, also possesses acceptable safety (e.g. irritation and sensitization characteristics), as well as good aesthetic properties (e.g., does not feel greasy or tacky). Examples of suitable organic solvents include: propylene glycol, polyethylene glycol (220–600), polypropylene glycol (425–2025), glycerol, 1,2,4-butanetriol, sorbitol esters, 1,2,6-hexanetriol, ethanol, isopropanol, butanediol, glycerin, and mixtures thereof. The solvent can be in any derived amount, preferably from about 1% to about 20%, more preferably from about 2% to about 10%, of the composition.

Antiinflamatory Agents

If desired, antiinfamatories can be included in the compositions of the invention to enhance photoprotection benefits, particularly from UVA. Steroidal antiinflamatories can be represented by hydrocortisone; non-steroidal antiinflamatories by the oxicans, salicylates, acetic acid derivatives, fenamates, propionic acid derivatives, pyrazoles, substituted phenyl compounds, 2-naphthyl containing compounds, and the natural antiinflamatories illustrated by aloe vera. These are more fully outlined in U.S. Pat. No. 5,487,884, the entire contents of which are incorporated herein by reference.

Antioxidants

In addition to the ascorbic acid, the compositions of the invention can also contain other antioxidants including those well known to those experienced in the art. Representative antioxidants include Vitamin E, tocopheryl acetate, betaglucan, coenzyme Q10 (representative formula— $CH_3C_6(O)_2(OCH_3)_2[CH_2CH:C(CH_3)CH_2]_nH$, butylated hydroxytoluene (BHT), superoxide dismutose and the like.

Controlling the pH of the composition ensures that greater than 82% of the ascorbic acid remains in the protonated, uncharged form. Although not wishing to be bound by theory, it is believed that the protonated form of ascorbic acid used in the invention is important dermatologically for several reasons. First, this form removes thionic repulsion of the two oxygen groups, thus stabilizing the molecule. Second, because the protonated form of ascorbic acid is uncharged, entry into the skin (which itself has a pH of about 3–5) should be facilitated. Preferably, the pH of the final composition should be maintained within the range of 3.5 to 4.1. The pH of the liquid phase is preferably maintained at 8.2–8.9 and more preferably 8.6–8.9. Any cosmetically or pharmaceutically acceptable pH adjusting or buffering compounds can be used. Most preferred is triethanolamine though other compounds such as sodium hydroxide or ammonium hydroxide can be used.

The product of the invention can be prepared using good manufacturing techniques involved in the mixing and blending of cosmetic and pharmaceutical ingredients. Preferably, organic ingredients, such as the surfactants, the sunscreens, the emollients, stabilizers and organosoluble preservatives are emulsified in water along with the organoclay material. To this emulsion can be added the remaining ingredients and finally the pH can be adjusted to the desired level. While the compositions of the invention can be made generally in any order, it is important that the oil phase of the emulsion be established with the organoclay material therein. Mixing conditions such as temperature are within the grasp of the skill artisan. Some or all of the ingredients for the liquid phase can be blended and then emulsified as desired. For stability of the ascorbic acid, the liquid phase is normally prepared separately and shipped to the user with the ascorbic acid in powdered form for direct addition or in a two compartment container which upon breaking the seal between the two parts of the container allows the powder to be easily admixed with the liquid phase.

The following examples are for illustrative purposes only and are not intended to limit the scope of the claimed invention.

EXAMPLE 1

A stable ascorbic acid emulsion formulation containing organoclay can be prepared as a two-part system consisting of a powder phase containing powdered ascorbic acid and a liquid phase which phases are blended in a ratio of 5% powder phase providing 5% ascorbic acid to the final blend and 95% of the liquid phase.

In this example, a commercially available organoclay material Tixogel VSP having the following components can be used in the liquid phase:

| | |
|---|---|
| Cyclomethicone | 79.5% |
| Quaternium-18 Bentonite | 17.5% |
| Propylene Carbonate | 2.5% |
| Water | 0.5% |

The quaternium-18 Bentonite can be represented by the formula:

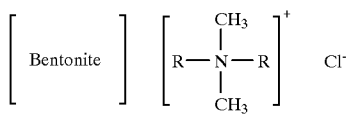

wherein R represents hydrogenated tallow fatty radicals.
The formula for cyclomethicone is

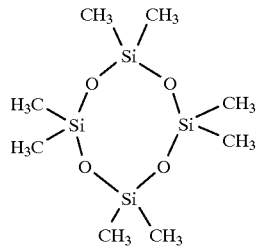

A typical liquid phase can be prepared from the following formulation:

| Liquid Phase Formulation | |
|---|---|
| | % W/W |
| PHASE A: | |
| Water | qs to 100.00 |
| pH adjustor-triethanolamine | 1.00 |
| PHASE B: | |
| Sunscreen | |
| Benzophenone | 4.00 |
| Octyl Methoxycinnamate | 7.50 |
| Emulsifiers | |
| Steareth-2 | 2.00 |
| Steareth-21 | 1.00 |
| Lecithin | 2.00 |
| Octyl Stearate | 2.00 |
| Glyceryl Stearate | 1.65 |
| PEG-100 Sterate | 1.25 |
| Tixogel VSP | 2.00 |
| PHASE C: | |
| Preservatives | |
| Phenoxyethanol | 0.60 |
| Methylparaben | 0.225 |
| Chlorphenesin | 0.225 |
| Solvents | |
| Butylene Glycol | 1.275 |
| Glycerin | 1.275 |

The liquid phase was prepared using the following manufacturing procedure:
STEP
1. Heat water of Phase A to 75–80° C. with rapid mixing.
2. Heat Phase B ingredients to 75–80° C. with rapid mixing.
3. At 75° C. add Phase B ingredients to Phase A water from Step 1 while mixing and homogenize for 10 minutes.
4. Cool bulk to 35° C. while mixing.
5. Add Phase C to bulk at 35° C. while mixing.
6. Cool bulk to 25° C.
7. Adjust pH to 8.6–8.9 with triethanolamine.

EXAMPLE 2

Example 2 demonstrates the preparation of the claimed composition and the stability of compositions to the invention.

A stable ascorbic acid emulsion formulation containing organoclay was prepared as a package consisting of a powder phase containing powdered ascorbic acid and a liquid phase which phases were blended in a ratio of 5% powder phase providing 5% ascorbic acid to the final and 95% of the liquid blend as in Example 1.

The liquid phase was prepared from the following formulation:

TABLE I

| | % W/W |
|---|---|
| PHASE A: | |
| Water (about 61%) | qs to 100.00000 (Total Composition) |
| Disodium EDTA | 0.10000 |
| Algae Extract | 4.00000 |
| Green Tea | 0.10000 |
| Triethanolamine | 1.00000 |
| PHASE B: | |
| Sodium Hyaluronate | 0.01500 |
| Water | 1.98500 |
| PHASE C: | |
| Benzophenone-3 | 4.00000 |
| Octyl Methoxycinnamate | 7.50000 |
| Tocopheryl Acetate | 0.10000 |
| BHT | 0.10000 |
| Coenzyme Q10 | 0.10000 |
| Betaglucan | 0.50000 |
| Steareth-2 | 2.00000 |
| Steareth-21 | 1.00000 |
| Lecithin | 2.00000 |
| Octyl Stearate | 2.00000 |
| Glyceryl Stearate | 1.65000 |
| PEG-1000 Stearate | 1.25000 |
| Phenyl Trimethicone | 1.70000 |
| Tixogel VSP | 2.00000 |
| Hydrogenated Vegetable Oil | 1.00000 |
| Dimethicone 200 (200 cst) | 1.00000 |
| PHASE D: | |
| Superoxide Dismutase | 0.10000 |
| PHASE E: | |
| Phenoxyethanol | 0.60000 |
| Methylparaben | 0.22500 |
| Butylene Glycol | 1.27500 |
| Glycerin | 1.27500 |
| Chlorphenesin | 0.22500 |
| Fragrance | 0.20000 |
| PHASE F: | |
| FD & C Yellow No. 5 | 0.00290 |
| D & C Orange No. 4 | 0.00126 |
| D & C Red No. 33 | 0.00084 |

STEP 1:
1. Charge a suitable container with water from Phase B and heat to 75–80° C., with rapid mixing.
2. Add sodium hyaluronate from Phase B slowly during mixing.
3. Continue mixing until solution is obtained.
4. Cool solution to 35° C.
STEP 2:
1. Heat water of Phase A to 75–80° C. with rapid mixing.
2. Add Phase A ingredients separately and mix until dissolved.
STEP 3:
1. Heat Phase C ingredients to 75–80° C. with rapid mixing.
2. At 75° C. add Phase C ingredients to Phase A from Step 2 while mixing and homogenize for 10 minutes.
3. Cool bulk to 35° C. while mixing.
4. Add Phase D to bulk at 35° C. while mixing.

5. Add Phases E and B at 35° C. while mixing.
6. Add Phase F while mixing at 35° C.
7. Cool bulk to 25° C.
8. Adjust pH to 8.6–8.9 with triethanolamine.
9. Cool bulk to 25° C. while mixing.

The ascorbic acid powder was then admixed with the liquid phase.

Following mixing, the ascorbic acid stability was determined by HPLC. The results compare the ascorbic acid assays at day 0 to days 5, 10, 15 and 25. After 25 days, more than 79% of the ascorbic remained in the liquid blend. Further, the physical appearance of the product had not deteriorated. The data are seen in Table II which follows:

TABLE II

|  | Assay - % Stability | Physical Appearance |
|---|---|---|
| Initial | 4.85% (100%) | Meets std. |
| 5 Days |  |  |
| 25° C. | 4.78% (98.6%) | 0 |
| 40° C. | 4.61% (95.1%) | 0 |
| 10 Days |  |  |
| 25° C. | 4.81% (99.2%) | 0 |
| 40° C. | 4.46% (92.0%) | 0 |
| 15 Days |  |  |
| 25° C. | 4.35% (89.7%) | 0 |
| 25 Days |  |  |
| 25° C. | 3.86% (79.6%) | 0 |

+3 Significant change in appearance
+2 Moderate change in appearance
+1 Slight change in appearance
0 No change in appearance As can be seen from the data, the physical appearance of the emulsion initially is acceptable and remains acceptable (no breaking of the emulsion) after 25 days. Without the organoclay ingredient, the emulsion would begin to break down after a few days, i.e., 2–3 days. In addition, the data shows that the ascorbic acid in the formulation remains stable for up to 15 days.

It will be appreciated that the instant specification and claims are set forth by way of illustration and not limitation, and that various modifications and changes may be made without departing from the spirit and scope of the invention.

What is claimed is:

1. A stabilized liquid water-in-oil emulsion composition containing from about 0.1% to about 20% by weight based on the total weight of the final composition of ascorbic acid comprising ascorbic acid, said ascorbic acid including its cosmetically/pharmaceutically acceptable salts or esters or reducing analogue thereof, and an emulsion stabilizingly effective amount of a liquid water-in-oil or water-in-oil-in-water emulsion phase containing an onium modified organoclay composition comprising a clay of the bentonite or montmorillonite or kaolinite group of clays or clay components thereof in combination with an onium clay-modifying compound, the organoclay composition being represented by the formula:

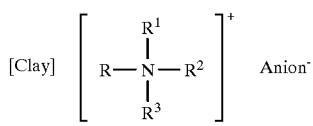

wherein the clay represents clays as defined above and wherein R represents a fatty radical of about 10 to about 20 carbon atoms; $R^1$, $R^2$, and $R^3$ representing independently R or a lower alkyl or hydroxyalkyl of 1 to about 4 carbon atoms.

2. A composition according to claim 1, wherein $R^1$ equals R and R is a tallow fatty alkyl radical.

3. A composition according to claim 1, wherein $R^2$ and $R^3$ are methyl.

4. A composition according to claim 1, wherein the organoclay composition is a montmorillonite or bentonite clay modified with a tallow ammonium chloride compound.

5. A composition according to claim 1, which further includes at least one of emollients, sunscreens, preservatives, antioxidants, antiinflamatories, emulsifiers, and optionally at least one of solvents, dyes and fragrances, and pH adjusting agents.

6. A combination comprising a powdered phase containing ascorbic acid, said ascorbic acid including its cosmetically/pharmaceutically acceptable salts or esters or reducing analogue thereof, and a liquid phase, the said liquid phase being a water-in-oil or oil-in-water emulsion, the powdered and liquid phases being adapted to be blended together, said liquid phase containing an emulsion stabilizingly effective amount of an onium modified organoclay composition comprising a clay of the bentonite or montmorillonite or kaolinite group of clays or clay components thereof in combination with a onium clay-modifying compound, the organoclay composition being represented by the formula:

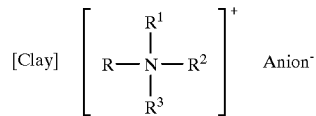

wherein the clay represents clays as defined above and wherein R represents a fatty radical of about 10 to about 20 carbon atoms; $R^1$, $R^2$, and $R^3$ representing independently R or a lower alkyl or hydroxyalkyl of 1 to about 4 carbon atoms.

7. A combination according to claim 6, wherein $R^1$ equals R and R is a tallow fatty alkyl radical.

8. A combination according to claim 6, wherein $R^2$ and $R^3$ are methyl.

9. A combination according to claim 6, wherein the organoclay composition is a montmorillonite or bentonite clay modified with a tallow ammonium chloride compound.

10. A combination according to claim 6, which further includes at least one of emollients, sunscreens, preservatives, antioxidants, antiinflamatories, emulsifiers, and optionally at least one of solvents, dyes and fragrances, and pH adjusting agents.

11. A topical/pharmaceutical stabilized liquid water-in-oil emulsion composition comprising from about 0.1% to about 20% by weight based on the total weight of the final composition of ascorbic acid, said ascorbic acid including its cosmetically/pharmaceutically acceptable salts or esters or reducing analogue thereof, and a liquid water-in-oil or water-in-oil-in-water emulsion containing an emulsion stabilizingly effective amount of an organoclay composition, said organoclay composition comprising a clay of the bentonite or montmorillonite or kaolinite group of clays or clay components thereof in combination with an onium modifier for said clay, the organoclay composition being represented by the formula:

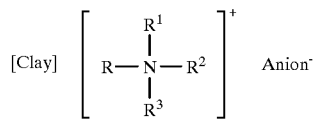

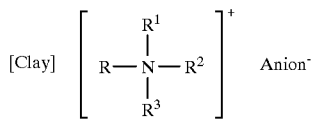

wherein the clay represents clays as defined above and wherein R represents a fatty radical of about 10 to about 20 carbon atoms; $R^1$, $R^2$, and $R^3$ representing independently R or a lower alkyl or hydroxyalkyl of 1 to about 4 carbon atoms.

12. A composition according to claim 11, wherein $R^1$ equals R and R represents a tallow fatty alkyl radical.

13. A composition according to claim 11, wherein $R^2$ and $R^3$ are methyl.

14. A composition according to claim 11, wherein the organoclay composition is a montmorillonite or bentonite clay modified with a tallow ammonium chloride compound.

15. A composition according to claim 11, which further includes at least one of emollients, sunscreens, preservatives, antioxidants, antiinflamatories, emulsifiers, and optionally at least one of solvents, dyes and fragrances and pH adjusting agents.

16. A method for stabilizing ascorbic acid, said ascorbic acid including its cosmetically/pharmaceutically acceptable salts or esters or reducing analogue thereof, in a liquid water-in-oil or water-in-oil-in-water emulsion comprising contacting the ascorbic acid in the liquid water-in-oil or water-in-oil-in-water emulsion with an emulsion stabilizingly effective amount of an onium modified organoclay composition comprising a clay of the bentonite or montmorillonite or kaolinite group of clays or clay components thereof and onium clay-modifying compound, the organoclay composition being represented by the formula:

wherein the clay represents clays as defined above and wherein R represents a fatty radical of about 10 to about 20 carbon atoms; $R^1$, $R^2$, and $R^3$ representing independently R or a lower alkyl or hydroxyalkyl of 1 to about 4 carbon atoms.

17. A method according to claim 16, wherein $R^1$ equals R and R is a tallow fatty alkyl radical.

18. A method according to claim 16, wherein $R^2$ and $R^3$ are methyl.

19. A method according to claim 16, wherein the organoclay composition is a montmorillonite or bentonite clay modified with a tallow ammonium chloride compound.

20. A method according to claim 16, which further includes at least one of emollients, sunscreens, preservatives, antioxidants, antiinflamatories, emulsifiers, and optionally at least one of solvents, dyes and fragrances, and pH adjusting agents.

21. A composition according to claim 1, wherein the ascorbic acid remains stable for two weeks.

22. A composition according to claim 11, wherein the ascorbic acid remains stable for two weeks.

23. A composition according to claim 6, wherein the ascorbic acid is present in an amount ranging from 1 to about 20 wt. %.

24. A composition according to claim 6, wherein the powdered phase and the liquid phase are blended together at the point of use.

* * * * *